United States Patent
Reed et al.

(10) Patent No.: US 9,918,921 B2
(45) Date of Patent: *Mar. 20, 2018

(54) METHODS FOR SHAPING FIBROUS MATERIAL AND TREATMENT COMPOSITIONS THEREFOR

(71) Applicant: The Procter & Gamble Company, Cincinnati, OH (US)

(72) Inventors: Jamie Angel Reed, Maineville, OH (US); Stevan A Samuel, Cincinnati, OH (US); Randy Purnell Washington, West Chester, OH (US); Alan David Willey, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/552,574

(22) Filed: Nov. 25, 2014

(65) Prior Publication Data

US 2015/0174035 A1 Jun. 25, 2015

Related U.S. Application Data

(60) Provisional application No. 61/918,215, filed on Dec. 19, 2013.

(51) Int. Cl.

| | | |
|---|---|---|
| *A61K 31/70* | (2006.01) | |
| *A61D 7/00* | (2006.01) | |
| *A61K 8/60* | (2006.01) | |
| *A45D 7/04* | (2006.01) | |
| *A45D 7/06* | (2006.01) | |
| *A61Q 5/00* | (2006.01) | |
| *A61Q 5/04* | (2006.01) | |
| *B29C 35/00* | (2006.01) | |
| *C11D 3/00* | (2006.01) | |
| *A61K 8/49* | (2006.01) | |
| *A61Q 1/10* | (2006.01) | |

(52) U.S. Cl.
CPC ............... *A61K 8/60* (2013.01); *A45D 7/04* (2013.01); *A45D 7/06* (2013.01); *A61K 8/4926* (2013.01); *A61K 8/602* (2013.01); *A61Q 1/10* (2013.01); *A61Q 5/00* (2013.01); *A61Q 5/04* (2013.01); *B29C 35/00* (2013.01); *C11D 3/0063* (2013.01); *A61K 2800/81* (2013.01); *A61K 2800/88* (2013.01); *B29K 2289/00* (2013.01)

(58) Field of Classification Search
CPC ...... C11D 3/0063; C11D 11/0017; A61Q 5/04
See application file for complete search history.

(56) References Cited

U.S. PATENT DOCUMENTS

| | | |
|---|---|---|
| 3,886,201 A | 5/1975 | Falk |
| 4,763,425 A | 8/1988 | Grennan |
| 4,793,993 A | 12/1988 | Edelstein et al. |
| 5,602,092 A | 2/1997 | Repinec, Jr. |
| 5,858,179 A | 1/1999 | Loda |
| 5,968,286 A | 10/1999 | Bergmann et al. |
| 6,060,471 A | 5/2000 | Handelman |
| 6,177,523 B1 | 1/2001 | Reich |
| 6,613,733 B1* | 9/2003 | Barnabas ............... C11D 3/221 510/276 |
| 7,550,136 B2 | 6/2009 | Cannon et al. |
| 7,815,900 B1 | 10/2010 | Cannell |
| 7,833,541 B2 | 11/2010 | Chekh et al. |
| 8,273,335 B2 | 9/2012 | Brownbill et al. |
| 8,349,780 B2 | 1/2013 | Baker |
| 8,475,777 B2 | 7/2013 | Rautschek |
| 8,513,200 B2 | 8/2013 | Dixon |
| 8,697,143 B2 | 4/2014 | Cannell et al. |
| 8,883,710 B2 | 11/2014 | Willey |
| 9,255,184 B2 | 2/2016 | Paul |
| 2005/0048018 A1 | 3/2005 | Fadeeva |
| 2005/0196372 A1 | 9/2005 | Cajan et al. |
| 2005/0241075 A1 | 11/2005 | Livoreil et al. |
| 2006/0257344 A1 | 11/2006 | Nguyen |
| 2007/0286837 A1 | 12/2007 | Torgerson et al. |
| 2008/0292574 A1 | 11/2008 | Euhara et al. |
| 2009/0145452 A1 | 6/2009 | Anderson et al. |
| 2009/0216012 A1 | 8/2009 | Maciuk et al. |
| 2009/0217547 A1 | 9/2009 | Kim |

(Continued)

FOREIGN PATENT DOCUMENTS

| | | |
|---|---|---|
| BR | 200503615 | 11/2006 |
| CA | 2562330 | 4/2008 |

(Continued)

OTHER PUBLICATIONS

International Search Report and Written Opinion, U.S. Appl. No. 14/552,603, dated Feb. 13, 2015, 7 pgs.
International Search Report and Written Opinion, U.S. Appl. No. 14/552,583, dated Feb. 13, 2015, 7 pgs.
International Search Report and Written Opinion, U.S. Appl. No. 14/552,566, dated Feb. 24, 2015, 7 pgs.
International Search Report and Written Opinion, U.S. Appl. No. 14/552,574, dated Feb. 24, 2015, 7 pgs.
International Search Report and Written Opinion, U.S. Appl. No. 14/552,578, dated Feb. 13, 2015, 7 pgs.
U.S. Appl. No. 14/552,566, filed Nov. 25, 2014, Jacob Robert Adams et al.

(Continued)

*Primary Examiner* — Gina C Justice
(74) *Attorney, Agent, or Firm* — Jason J Camp

(57) ABSTRACT

The present invention relates to a method of shaping a fibrous material and treatment compositions therefor. The method comprises providing a treatment composition comprising an active agent and a photocatalyst, applying the treatment composition to the fibrous material to form a treated fibrous material, mechanically shaping the treated fibrous material, and exposing the treated fibrous material to electromagnetic radiation. The treatment composition comprises an active agent, wherein the active agent comprises a sugar; and a photocatalyst.

23 Claims, 3 Drawing Sheets

(56) References Cited

U.S. PATENT DOCUMENTS

| | | |
|---|---|---|
| 2009/0285768 A1* | 11/2009 | Baker .................... A61K 8/361 424/59 |
| 2009/0320869 A1 | 12/2009 | Fadeeva |
| 2010/0101598 A1 | 4/2010 | Maddocks et al. |
| 2010/0310491 A1 | 12/2010 | Falk et al. |
| 2011/0256083 A1 | 10/2011 | Smith |
| 2011/0318295 A1 | 12/2011 | Shimizu et al. |
| 2012/0093755 A1 | 4/2012 | Humphreys |
| 2012/0192888 A1 | 8/2012 | Barbarat et al. |
| 2013/0164248 A1 | 6/2013 | Khenniche |
| 2013/0319449 A1 | 12/2013 | Xavier |
| 2014/0186283 A1 | 7/2014 | Cabourg et al. |
| 2014/0196741 A1 | 7/2014 | Cabourg et al. |
| 2015/0096584 A1 | 4/2015 | Washington |
| 2015/0173478 A1 | 6/2015 | Adams |
| 2015/0173479 A1 | 6/2015 | Adams |
| 2015/0173480 A1 | 6/2015 | Washington |
| 2015/0174023 A1 | 6/2015 | Washington |
| 2015/0174027 A1 | 6/2015 | Washington |
| 2015/0174028 A1 | 6/2015 | Washington |
| 2015/0174029 A1 | 6/2015 | Washington |
| 2015/0174030 A1 | 6/2015 | Washington |
| 2015/0174031 A1 | 6/2015 | Washington |
| 2015/0174032 A1 | 6/2015 | Washington |
| 2015/0174036 A1 | 6/2015 | Washington |
| 2015/0174037 A1 | 6/2015 | Washington |
| 2015/0174432 A1 | 6/2015 | Adams |
| 2015/0174793 A1 | 6/2015 | Adams |
| 2015/0374604 A1 | 12/2015 | Kadir |

FOREIGN PATENT DOCUMENTS

| | | |
|---|---|---|
| CN | 201504727 | 6/2010 |
| DE | 102005059936 A1 | 10/2006 |
| EP | 1900393 | 3/2008 |
| FR | 2950247 B1 | 2/2012 |
| GB | 1267846 | 3/1972 |
| GB | 1376136 A | 12/1974 |
| WO | WO2007048472 | 5/2007 |
| WO | WO 2009140076 A1 | 11/2009 |
| WO | WO2010067323 | 6/2010 |
| WO | WO2011074143 | 6/2011 |
| WO | WO 2012169077 A1 | 12/2012 |
| WO | WO2012027369 | 3/2013 |
| WO | WO2013145330 A1 | 10/2013 |

OTHER PUBLICATIONS

U.S. Appl. No. 14/552,603, filed Nov. 25, 2014, Jacob Robert Adams et al.

U.S. Appl. No. 14/552,578, filed Nov. 25, 2014, Jacob Robert Adams et al.

U.S. Appl. No. 14/552,583, filed Nov. 25, 2014, Jacob Robert Adams et al.

* cited by examiner

METHODS FOR SHAPING FIBROUS MATERIAL AND TREATMENT COMPOSITIONS THEREFOR

FIELD OF THE INVENTION

The present invention relates to methods for shaping fibrous materials, such as hair or fabrics, and treatment compositions comprising an active agent and a photocatalyst. The treatment composition is applied to the fibrous material. The treated fibrous material is mechanically shaped and exposed to electromagnetic radiation resulting in a fibrous material that is shaped semi-permanently.

BACKGROUND OF THE INVENTION

Consumer products for treating fibrous materials, such as hair and fabrics, are a staple in most households. Such products provide a variety of benefits, including cleaning benefits, styling benefits, wrinkle removal, and the like.

In the field of hair care products, consumers are constantly demanding products that meet their daily styling needs, such as straightening hair or curling hair, without damaging the hair. The perceived and sometimes real impact of various treatments and the implements such as blow drying and flat iron can have detrimental effects on the acute and chronic nature of hair.

Permanent methods, such as hair relaxers, usually comprise the steps of applying onto hair a composition comprising a high pH solution (or combination of components to generate high pH), leaving on for a protracted time and then applying a neutralizing composition. A relaxer is a treatment predominately used by people having naturally curly hair to permanently straighten hair. The treatment relies on either the one-step sodium hydroxide (lye) or a two step (e.g. guanidine carbonate and calcium hydroxide) to achieve very high pH (pH 12-14).

Semi-permanent benefits can be achieved using redox chemistry such as thioglycolic acid (TGA) and hydrogen peroxide. Here, the curly hair is transformed into the straight hair because the disulfide bonds are broken by the reaction with TGA. The straighter style is locked in during the oxidation step with hydrogen peroxide.

Non-permanent methods usually comprise the step of heating the hair with a flat-iron or heating element. Methods using such devices in combination with chemically-modifying the internal hair fibres can obtain long-lasting effects e.g. over several months. The Brazilian Keratin Treatments (BKTs) enable the achievement of a straight hairstyle that lasts several months. The key active in BKTs is formaldehyde. The most efficacious treatments (used mainly in salons) rely on high temperature—usually 232° C. (450° F.)—with formaldehyde. Hair treated with products with high concentration of formaldehyde such as Brazilian Blowout delivers semi-permanent straight hair. Over time and following shampooing, the hair reverts back to a curly configuration.

The known methods for straightening or curling hair all have drawbacks. The permanent methods are typically time-consuming and may damage hair.

In the field of fabric care products, consumers desire products that can be used to impart a particular durable or semi-permanent shape to the fabrics, whether it be straightening fabrics (such as in removing wrinkles from fabrics) or imparting creases in fabrics (such as in creasing trousers or shirts). Such products used to impart such shape to fabrics typically involve the use of high heat (e.g. 275-450 F) such as using a heated clothes iron. Products are used in conjunction with a heated iron, such as spray starch or the like. The use of a heated iron and associated products can, over time, lead to degradation of the fabrics and can yield fabrics that have an unpleasant hand feel (e.g. being overly stiff). In addition, subsequent washing of the fabrics will tend to remove the previously imparted shape to the fabrics.

There is a need therefore for providing a method for shaping a fibrous material, such as hair or fabrics. Further, there is a need for doing so without unduly damaging the fibrous material being shaped.

SUMMARY OF THE INVENTION

The present invention relates to a method for shaping fibrous material, the method comprising providing a treatment composition comprising an active agent and a photocatalyst, applying the treatment composition to the fibrous material to form a treated fibrous material, mechanically shaping the treated fibrous material, and exposing the treated fibrous material to electromagnetic radiation, preferably having a wavelength of from about 300 nanometers ("nm") to about 750 nm.

The present invention further relates to a treatment composition for shaping fibrous material comprising an active agent, wherein the active agent comprises a sugar; and a photocatalyst. The treatment composition optionally further comprises a carrier and other optional components.

The present invention further relates to a kit comprising the treatment composition and an appliance for mechanically shaping the fibrous material, preferably wherein the appliance comprises a lighted element.

DETAILED DESCRIPTION OF THE INVENTION

Figure 1:
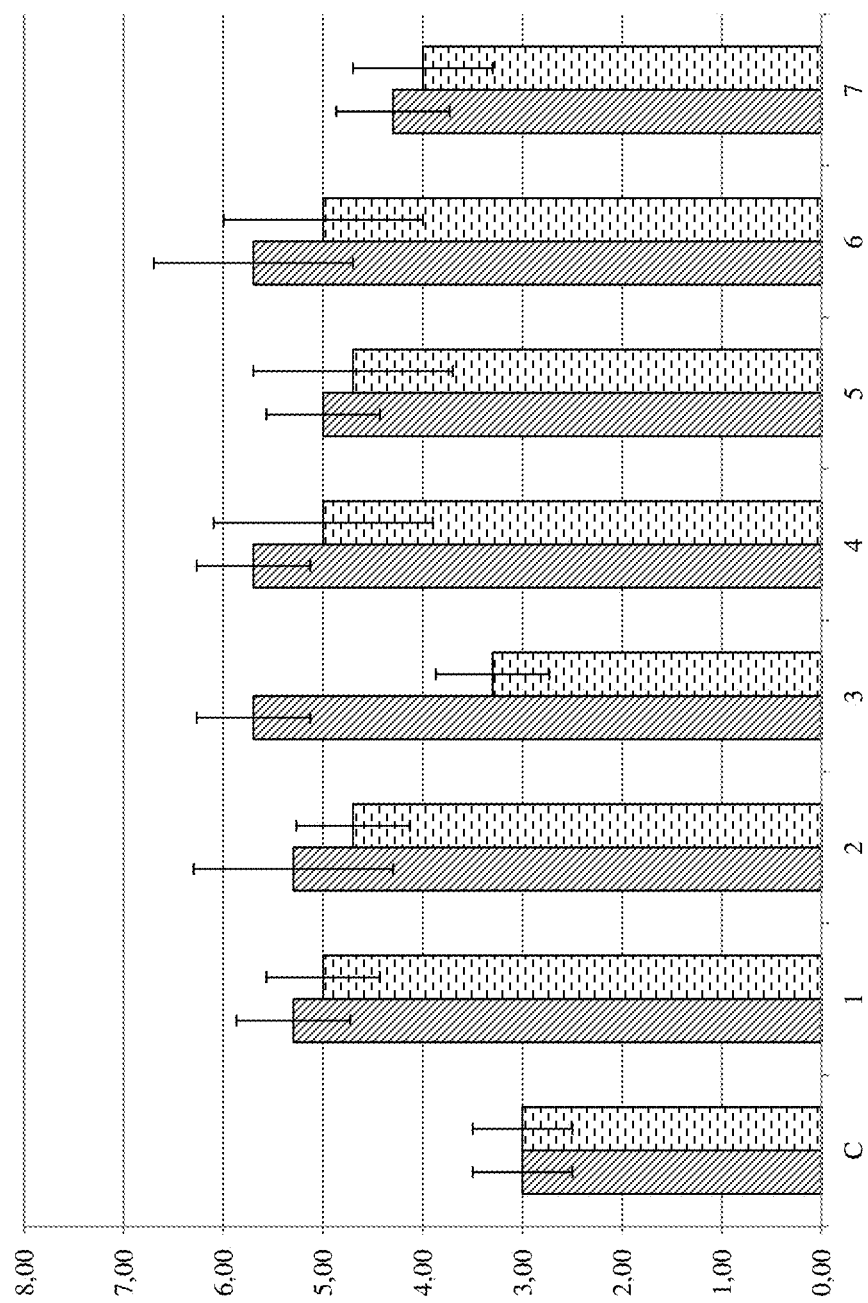
FIG. 1 is a bar chart illustrating hair straightening results for various treatment compositions of the present invention versus a control.

As used herein, the term "functional group" means an atom or group of associated atoms that, at least in part, defines the structure and determines the properties of a particular family of chemical compounds. A functional group may be a region on or in a molecule or material that is a site of specific chemical reactivity compared to other regions of the molecule or material. Functional groups generally have characteristic properties and may control, in part, the reactivity of a molecule as a whole. Functional groups include, but are not limited to, hydroxyl groups, thiol groups, carbonyl groups, carboxyl groups, sulfonate groups, sulfide groups, ether groups, halogen atoms, amino groups, cyano groups, nitro groups, and the like. Compounds that are generally classified (structurally and/or functionally) according to functional groups include, but are not limited to, alkanes, alkenes, alkynes, aromatic compounds, halides, alcohols, ethers, esters, amines, imines, imides, carboxylic acids, amides, acid halides, acid anhydrides, nitriles, ketones, aldehydes, carbonates, peroxides, hydroperoxides, carbohydrates, acetals, epoxides, sulfonic acids, sulfonate esters, sulfides, sulfoxides, thioethers, thiocyanates, disulfides, phosphonic acids, phosphate esters, phosphines, azides, azo compounds, nitro compounds, nitrates, nitriles, nitrites, nitroso compounds, thiols, cyanates, isocyanates, acetals, and ketals, for example.

The term "active agent" as used herein means substances which can react with a photoactivated photoactivator in order to impart a desired shape of the fibrous material. This may include, for example, imparting a crease to a fabric, removing wrinkles from a fabric, straightening hair, curling hair, curling eyelashes, and the like.

The term "suitable for application to human hair" and "suitable for application to human skin" as used herein means that the compositions or components thereof so described are suitable for use in contact with human hair, human scalp, human eyelashes, and human skin without undue toxicity, incompatibility, instability, allergic response, and the like.

The term "fibrous material" as used herein means a material that comprises fibers or materials that are fibers themselves. Fibrous materials include keratin fibers (such as hair or eyelashes), cellulosic fibers (e.g. wood fibers, pulp fibers, cotton fibers, hemp fibers, silk fibers, rayon fibers, lyocell fibers, and the like), synthetic fibers (e.g. polyethylene fibers, polypropylene fibers, polyester fibers, bicomponent fibers, and the like), and combinations thereof. Fibrous materials further include woven materials and nonwoven materials that contain fibers, such as clothing or textile fabrics.

The term "consumer product" as used herein means a personal care product or a household care product. Consumer products are typically sold in grocery stores, drug stores, and the like.

The term "personal care product" as used herein means a product such as, for example, cosmetic products for treating eyelashes such as mascara; hair care products such as mousse, hair spray, styling gel, shampoo, hair conditioner (leave-in or rinse-out), cream rinse, hair dye, hair coloring product, hair shine product, hair serum, hair anti-frizz product, hair split-end repair product, permanent waving solution, antidandruff formulation, and the like.

The term "household care product" as used herein means a product such as, for example, a laundry detergent, a fabric conditioner, a fabric dye, a laundry additive, a fabric surface protectant, a fabric refresher spray, a fabric wrinkle reducing spray, a vehicle seat fabric treatment, upholstery treatment, carpet treatment, and the like. Household care products may be in the form of liquids, gels, suspensions, powders, sheets, and the like. Household care products may also be for household or home care use as well as for professional, commercial and/or industrial use.

It is believed that the compositions and methods described herein provide for the modification of the bulk properties of a fibrous material by treating the material with an active agent capable of penetrating the fibers of, reacting with, and covalently binding to, the fibrous material. Such modification of the bulk properties generally relate to the three dimensional profile of the fibrous material (i.e. curly/straight or wrinkled/straight (or flat)).

The various aspects relate, in general, to compositions and methods for treating a fibrous material including, but not limited to, physiological fibrous materials such as, for example, hair fibers, as well as non-physiological fibrous materials such as, for example, fabric, paper, and the like. Substrates may also include surfaces that have been previously modified such as, for example, coated surfaces. The terms "substrate" and "material" may be used interchangeably in the context of fibrous material to be modified by the compositions and methods described herein.

In various aspects, the compositions described herein include an active agent that can modify a fibrous material in the presence of an acid or a base, a photocatalyst capable of generating an acid or a base upon exposure to light, and optionally a suitable carrier, which may be water. In various aspects, the compositions described herein may also include one or more optional components, including surfactants, emulsifiers, oxidants, reductants, pH regulators, emollients, humectants, proteins, peptides, amino acids, additive polymers, glossers, essential oils and/or fatty acids, lubricants, sequestrants/chelators, antistatic agents, rheology modifiers, feel agents, fillers, preservatives, perfumes, other functional components, or combinations thereof.

Generally, attachment of active agents on fibrous materials such as hair and fabric, for example, often proves difficult to achieve. This is especially true in the presence of water, which may rapidly degrade reactive moieties before reaction with the substrate occurs. Moreover, aqueous media are known to chemically facilitate hydrolysis and oxidation reactions that may compete against covalent attachment of active agents to fibrous materials. This may pose particular problems, for example, in personal care products where water is often used as a physiologically acceptable carrier. Household care products also often use water in a variety of capacities, most notably as a solvent or diluent.

In addition, fibrous substrates such as, for example, hair, and fabric may not contain particularly reactive chemical functional groups on the interior that would readily react with active components to form covalent bonds. This relatively low substrate reactivity may result in a reaction system that is outside the practical time frame of an apply-and-rinse environment (e.g., shampooing and conditioning hair, laundering fabrics, or the like). The various aspects of the compositions and methods described herein are directed toward a photocatalyst technology that allows the use of light to promote a reaction such as, for example, the attachment of an active agent to the fibers of a fibrous substrate, thereby overcoming said relatively low substrate reactivity.

In various aspects, the active agents may be one or more small molecules with a molecular weight of below about 1000 g/mol that further react to form higher molecular weight species once having penetrated the fibers of the fibrous material in the presence of acid or base. The fibrous material is treated with a composition comprising a photocatalyst and an active agent, which at least partially penetrates the fibers. Upon exposure to light, the photocatalyst is activated thereby generating acid or base, which catalyzes the reaction of the small molecule, thereby attaching to the fiber and/or forming a higher molecular weight species.

In various aspects of the compositions and methods described herein, the photocatalyst may be a photoacid that liberates a proton upon exposure to light. The proton (which may be solvated, e.g., in the form of a hydronium ion) may catalyze the formation of a covalent bond. In various embodiments of the compositions and methods described herein, the photocatalyst may be a photobase that liberates a hydroxide anion upon exposure to light. The hydroxide anion may catalyze the formation of a covalent bond. In various embodiments, the mechanism of action of a photoacid or photobase is not limited to an Arrhenius-type or Brønsted-Lowry type acid or base system, but rather may also include a Lewis-type acid or base that is catalytically activated upon exposure to light. The compositions and methods described herein are not limited in this context.

Acid or base catalysis reactions are generally impracticable in the context of personal care products because it is difficult to generate sufficient acid or base concentration at the surface or within the bulk of the substrate without having relatively high or relatively low pH. The use of products having relatively high or relatively low pH is generally inappropriate because such acidic and caustic substances may be physiologically unacceptable. The use of relatively high or relatively low pH can also be undesireable in the context of household care products, such as laundry detergent, because such acidic and caustic substances may cause undue damage to fabrics.

The compositions and methods described herein overcome these limitations. It is believed that the use of a photocatalyst allows for the co-localization of the catalyst and an active component within the fibers of the substrate material. The photocatalyst however is not activated until it is exposed to light. Photoacid catalysts, for example, exhibit a decrease in pKa upon exposure to light of suitable wavelength. Photobase catalysts, for example, may exhibit an increase in pKb upon exposure to light of a suitable wavelength. The respective increase in acid or base strength upon exposure to light results in a localized increase in proton or hydroxide concentration within the substrate fibers which facilitates rapid reaction, for example. Moreover, because the proton or hydroxide concentration is localized at, near or within the substrate for a short period of time (before diffusing into the surrounding medium), bulk pH may be essentially unaffected by the photocatalytic reaction and may remain close to neutral, given the quantity of the photocatalyst used. This is advantageous for physiological applications such as, for example, in personal care products and in various consumer care product applications. In addition, the transient localized nature of the acidic or basic catalysis also contributes to the stability of the covalent bond formed during the process in cases where the covalent bond is sensitive to high or low pH.

Therefore, photocatalysis of the reactions forming covalent bonds between active components and fibrous substrates in the various embodiments of the compositions and methods described herein provides for an efficient, controllable, stable and physiologically acceptable approach to substrate treatment.

The fibrous material to be shaped by the methods and compositions of the present invention may be treated by spraying, soaking, spreading, coating, rinsing, or any other suitable means of introducing the composition into the bulk of the fibrous material. In some aspects, it can be important to ensure the entire substrate is wetted by the treatment composition in order to ensure sufficient modification of the fibrous material. If the active agent is at least partially insoluble in the carrier, it can be important to maximize contact between the active agent and the fibrous material by, for example, minimizing the drop size or particle size of the active agent in the carrier. In various aspects, it may be desired to introduce the treatment composition onto only a single portion or multiple portions of the fibrous material. In other aspects, it may be desired to irradiate only a single portion or multiple portions of a fibrous material with electromagnetic radiation of a wavelength suitable to activate the photocatalyst. This allows for control of the location and extent of the surface and/or bulk modification.

Each of the various components of the compositions and associated methods described herein, as well as preferred and optional components, are described in detail.

Treatment Composition

The treatment composition of the present invention comprises an active agent and a photocatalyst. The treatment composition optionally further comprises a carrier. For purposes of the present invention, treatment compositions encompass concentrated compositions for subsequent dilution before use, as well as diluted compositions that are ready for use.

Active Agent

The active agent of the present invention comprises a sugar. Sugars are useful because they are naturally-derived, which can be preferred by consumers versus synthetic compounds. This is not only for perceived health and sensitivity reasons, but also for sustainability and environmental reasons—sugars break down naturally and quickly and do not require special disposal methods. Furthermore, sugars are also easy to source and relatively inexpensive.

In at least one aspect, the treatment composition comprises sucrose. In at least one aspect, the sugar is a glucoside. In at least one aspect, the sugar is methyl glucoside. In at least one aspect, the sugar is a disaccharide. In at least one aspect, the sugar is sucrose.

In at least one aspect, the active agent is a monosaccharide. In at least one aspect, the sugar is a monosaccharide and wherein the treatment composition comprises from about 0.1% to about 40%, or from about 0.5% to about 20%, or from about 1% to about 15%, or from about 7% to about 20%, or from about 8% to about 19%, or from about 10% to about 18% monosaccharide. In at least one aspect, the active agent is a pentose or a hexose. In at least one aspect, the active agent is a reducing sugar. In at least one aspect, the treatment composition comprises from about 7% to about 20%, or from about 8% to about 19%, or from about 10% to about 18% reducing sugar. In at least one aspect, the treatment composition comprises from about 12% to about 18% reducing sugar. In at least one aspect, the treatment composition comprises a reducing sugar and wherein, if the treatment composition is heated to a temperature of 100° C., the treatment composition comprises from about 12% to about 18% reducing sugar. In at least one aspect, the treatment composition comprises a total amount of reducing sugar being from about 12% to about 18% reducing sugar.

As used herein, "reducing sugar" means any sugar that either has an aldehyde group or is capable of forming an aldehyde group in solution through isomerism, and that gives a positive result in the Benedict's test. An aldehyde group is —C(═O)H. The Benedict's test involves employment of the Benedict's solution. The Benedict's solution is available from Sigma Aldrich as 'Benedict's Reagent', which comprises sodium carbonate, copper sulphate pentahydrate and 2,5-difluorotoluene. In the Benedict's test, 1 mL of Benedict's solution is added to a 20 mL of 5% aqueous solution comprising a dissolved test compound. Benedict's solution contains blue copper(II) ions ($Cu^{2+}$). The solution is heated to 80° C. for 15 min and the resulting colour change is noted. The cupric ion of the Benedict's solution is reduced to cuprous ion by the aldehyde of the sugar. A positive Benedict's test result is confirmed with a change in colour as cupric ions ($Cu^{2+}$) are converted to cuprous ions i.e. reduced to copper(I) ions ($Cu^+$). These are precipitated as red copper (I) oxide which is insoluble in water. The test is also designed for longer heating time and higher temperature to note any colour change. The solution may range in colour (with increasing amounts of reducing sugar) from green, through yellow and orange, to red. Any colour change away from blue suggest levels of reducing sugar. The wavelength of light reflected by the solution will change with the colour. In at least one aspect, a positive Benedict's test result is when the solution emits light not peaking with a wavelength in the range of 450 nm to 495 nm. In at least one aspect, a positive Benedict's test result is when the solution emits light peaking with a wavelength in the range of 620 nm to 750 nm. This can be measured using a spectrophotometer.

TABLE 1

Assessment of sugars using the Benedict's Test

| Sugar | 80° C., 15 min | 100° C., 40 min |
|---|---|---|
| Control solution* | Negative | Negative |
| Ribose | Positive | Positive |
| Arabinose | Positive | Positive |
| Glucose | Positive | Positive |
| Fructose | Positive | Positive |
| Xylose | Positive | Positive |
| Sucrose | Negative | Positive |
| Methyl glucoside | Negative | Positive |

*Benedict's solution only.

In the art, the Benedict's reagent is used as a test for the presence of reducing sugars. This includes all monosaccharides and many disaccharides, including lactose and maltose. Even more generally, Benedict's test will detect the presence of aldehydes, and alpha-hydroxy-ketones, including those that occur in certain ketoses. Thus, although fructose, a ketose, is not strictly a reducing sugar, it is an alpha-hydroxy-ketone, it gives a positive test because it is converted to the aldoses glucose and mannose by the base in the reagent. The copper sulphate in Benedict's solution reacts with reducing sugars. One liter of Benedict's reagent can be prepared from 100 g of anhydrous sodium carbonate, 173 g of sodium citrate and 17.3 g of copper(II) sulfate pentahydrate. Benedict's Reagent provides a quantitative test for reducing sugars along with qualitative test. The colour of the obtained precipitate gives an idea about the quantity of sugar present in the solution. A greenish precipitate indicates about 0.5% concentration; yellow precipitate indicates 1% concentration; orange indicates 1.5% and red indicates 2% or higher concentration. A positive result in the Benedict's test can be recognised for a compound by a 5% (weight/weight) solution of compound in water as a red colouring. The aldehyde group of the sugar allows the sugar to act as a reducing agent, for example in the Benedict's test.

In at least one aspect, the reducing sugar is selected from the group consisting of: ribose, arabinose, xylose, lyxose, galactose, mannose, and mixtures thereof. In at least one aspect, the reducing sugar is fructose or glucose. Sugars and reducing sugars are available from Sigma Aldrich. In at least one aspect, the reducing sugar is ribose, arabinose, or a mixture thereof. In at least one aspect, the treatment composition comprises a reducing sugar and wherein the reducing sugar is selected from the group consisting of: arabinose, ribose, and mixtures thereof. In at least one aspect, the treatment composition comprises a reducing sugar and wherein the reducing sugar is selected from the group consisting of: D-arabinose, L-arabinose, and mixtures thereof. In at least one aspect, the reducing sugar is L-arabinose. In at least one aspect, the sole reducing sugar is a pentose. In at least one aspect, the sole reducing sugar is selected from the group consisting of: arabinose, ribose, and mixtures thereof. The reducing sugars arabinose, ribose, and mixtures thereof have the benefit of excellent hair straightening performance. By treating hair with reducing sugar and subsequent treatment as per the invention the treated hair becomes durably straight. Arabinose and ribose are 5 carbon sugars and these are found to have even better performance than sugars with other carbon numbers, such as 6 carbon and 7 carbon sugars. On the other hand, 6 carbon sugars are easily available and thus have economic advantages. In at least one aspect, the sugar is a reducing sugar and wherein the reducing sugar is selected from the group consisting of: ribose, arabinose, xylose, lyxose, galactose, mannose, and mixtures thereof; or the sugar is arabinose. In at least one aspect, the treatment composition comprises a total amount of reducing sugar being from about 12% to about 18% reducing sugar, and wherein the treatment composition comprises arabinose.

In at least one aspect, the sugar as an added ingredient in the treatment composition is not a reducing sugar (e.g. glucose, sucrose, and the like). In one aspect, the sugar is not a reducing sugar at any point during the method of the present invention (e.g. wherein the method of the present invention does not include a step of adding heat).

In at least one aspect, the active agent comprises at least one further functional group. In one aspect, the further functional group is any organic moiety comprising at least one of an oxygen, nitrogen, phosphorous, boron or sulfur atom. The further functional group can be selected from the group consisting of: hydroxyl, carbonyl, aldehyde, haloformyl, carbonate ester, carboxylate, carboxyl, ester, methoxy, hydroperoxy, peroxy, ether, hemiacetal, hemiketal, acetal, ketal, orthoester, orthocarbonate ester, carboxamide, primary amine, secondary amine, tertiary amine, ammonium, primary ketimine, secondary ketimine, primary aldimine, secondary aldimine, imide, azide, azo or diimide, cyanate, isocyanate, nitrate, nitrile, isonitrile, nitrosooxy, nitro, nitroso, pyridyl, sulfhydryl, sulfide, disulfide, sulfinyl, sulfonyl, sulfino, sulfo, thiocyanate, isothiocyanate, carbonothioyl, carbonothioyl, phosphino, phosphono, phosphate, borono, boronate, borino, borinate.

In at least one aspect, the active agent comprises at least two functional groups selected from the group consisting of —NH$_2$, —NH—, —SH, —OH, —C(=O)H, —C(=O)—, —SH, and —COOH.

The active agent herein has a molecular weight of below about 1000 g/mol, below about 750 g/mol, below about 500 g/mol, below about 300 g/mol, from about 50 g/mol to about 250 g/mol, or from about 80 g/mol to about 150 g/mol. It is believed that the relatively low molecular weight of the active agent facilitates penetration of the active agent into the fiber structure of the fibrous material, thereby allowing the fibrous material to be shaped by the method of the present invention.

The treatment composition of the present invention preferably comprises from about 0.1% to about 99.99%, from about 0.1% to about 40%, from about 0.1% to about 15%, from about 1% to about 10%, or from about 2% to about 7%, by weight of the treatment composition, of active agent.

Photocatalyst

The photocatalyst may be any photoacid or photobase (or conjugate thereof) having a pKa (or pKb) value that decreases (or increases) upon exposure to electromagnetic radiation. The electromagnetic radiation may be of any suitable wavelength to result in the respective decrease or increase in pKa or pKb, and preferably is in the range of from about 300 nm to about 750 nm. For example the electromagnetic radiation may be ambient light, sunlight, incandescent light, fluorescent light, LED light, laser light, solar light, and the like. The electromagnetic radiation may fall within any classification along the electromagnetic spectrum, but preferably is visible light. It will be readily apparent to one of ordinary skill in the art that the appropriate wavelength or wavelengths of light will be dependent upon the identities of the one or more photocatalysts employed.

In addition, the suitable light may be provided from any source capable of illuminating the fibrous material. For example, ambient sunlight, incandescent light, fluorescent light, and the like may provide electromagnetic radiation of suitable wavelength. Accordingly, the electromagnetic radiation may be provided by conventional sources such as lamps and portable or battery-powered lights. In addition, specific devices may be developed or adapted for use with the compositions and method described herein. For example, a hair brush configured to incorporate LEDs that provide light of a suitable wavelength may be used.

In various embodiments, the photocatalyst is a photoacid such as, for example, a hydroxylated aromatic compound (i.e. a hydroxyl-substituted aromatic compound), a sulfonated pyrene compound, an onium salt, a diazomethane derivative, a bissulfone derivative, a disulfuno derivative, a nitrobenzyl sulfonate derivate, a sulfonic acid ester derivative, a sulfonic acid ester of an N-hydroxyimide, or combinations thereof. The photoacid is preferably a hydroxyl-substituted aromatic compound.

Photoacid catalysts may include, for example, hydroxy-substituted aromatics such as, for example, 8-hydroxyquinoline, 8-hydroxyquinoline sulfate, 8-quinolinol-1-oxide, 5-hydroxyquinoline, 6-hydroxyquinoline, 7-hydroxyquinoline, 5-iodo-7-sulfo-8-hydroxyquinoline, 5-fluoro-8-hydroxyquinoline, 5-fluoro-7-chloro-8-hydroxyquinoline, 5-fluoro-7-bromo-8-hydroxyquinoline, 5-fluoro-7-iodo-8-hydroxyquinoline, 7-fluoro-8-hydroxyquinoline, 5-chloro-8-hydroxyquinoline, 5,7-dichloro-8-hydroxyquinoline, 5-chloro-7-brono-8-hydroxyquinoline, 5-chloro-7-iodo-8-hydroxyquinoline, 7-chloro-8-hydroxyquinoline, 5-bromo-8-hydroxyquinoline, 5-bromo-7-chloro-8-hydroxyquinoline, 5,7-dibromo-8-hydroxyquinoline, 5-bromo-7-iodo-8-hydroxyquinoline, 7-bromo-8-hydroxyquinoline, 5-iodo-8-hydroxyquinoline, 5-iodo-7-chloro-8-hydroxyquinoline, 5,7-diiodo-8-hydroxyquinoline, 7-iodo-8-hydroxyquinoline, 5-sulfonic acid-8-hydroxyquinoline, 7-sulfonic acid-8-hydroxyquinoline, 5-sulfonic acid-7-iodo-8-hydroxyquinoline, 5-thiocyano-8-hydroxyquinoline, 5-chloro-8-hydroxyquinoline, 5-bromo-8-hydroxyquinoline, 5,7-dibromo-8-hydroxyquinoline, 5-iodo-8-hydroxyquinoline, 5,7-diiodo-8-hydroxyquinoline, 7-azaindole, 7-cyano-2-naphthol, 8-cyano-2-naphthol, 5-cyano-2-naphthol, 1-hydroxy-3,6,8-pyrenetrisulfonic acid, Trans-3-hydroxystilbene, 2-hydroxymethylphenol, pelargonidin, or mixtures thereof.

Photoacid catalysts may include onium salts such as, for example, bis(4-tert-butylphenyl)iodonium perfluoro-1-butanesulfonate, diphenyliodonium perfluoro-1-butanesulfonate, diphenyliodonium-9,10-dimethoxyanthracene-2-sulfonate, diphenyliodonium hexafluorophosphate, diphenyliodonium nitrate, diphenyliodonium p-toluenesulfonate, diphenyliodonium triflate, (4-methylphenyl)diphenylsulfonium triflate, (4-methylthiophenyl)methyl phenyl sulfonium triflate, 2-naphthyl diphenylsulfonium triflate, (4-phenoxyphenyl)diphenylsulfonium triflate, (4-phenylthiophenyl)diphenylsulfonium triflate, thiobis(triphenyl sulfonium hexafluorophosphate), triarylsulfonium hexafluoroantimonate, triarylsulfonium hexafluorophosphate salt, triphenylsulfonium perfluoro-1-butanesulfonate, triphenylsulfonium triflate, tris(4-tert-butylphenyl) sulfonium perfluoro-1-butanesulfonate, tris(4-tert-butylphenyl)sulfonium triflate, bis(4-tert-butylphenyl)iodonium p-toluenesulfonate, bis(4-tert-butylphenyl)iodonium triflate, (4-bromophenyl) diphenylsulfonium triflate, (tert-butoxycarbonyl-methoxynaphthyl)diphenylsulfonium triflate, (tert-butoxycarbonylmethoxyphenyl)diphenylsulfonium triflate, (4-tert-butylphenyl)diphenylsulfonium triflate, (4-chlorophenyl) diphenylsulfonium triflate, (4-fluorophenyl) diphenylsulfonium triflate, [4-[2-hydroxytetradecyl)oxy] phenyl]phenyliodonium hexafluoroantimonate, (4-iodophenyl)diphenylsulfonium triflate, (4-methoxyphenyl)diphenylsulfonium triflate, diphenyliodo hexafluorophosphate, diphenyliodo hexafluoroarsenate, diphenyliodo hexafluoroantimonate, diphenyl p-methoxyphenyl triflate, diphenyl p-toluenyl triflate, diphenyl p-isobutylphenyl triflate, diphenyl p-t-butylphenyl triflate, triphenylsulfonium hexafluorophosphate, triphenylsulfonium hexafluoroarsenate, triphenylsulfonium hexafluoroantimonate, triphenylsulfonium triflate, dibutylnaphthyl sulfonium triflate, diphenyliodonium trifluoromethanesulfonate, (p-tert-butoxyphenyl) phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)-sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl) sulfonium p-toluenesulfonate, triphenylsulfonium nonafluorobutanesulfonate, triphenylsulfonium butanesulfonate, trimethyl-sulfonium trifluoromethanesulfonate, trimethylsulfonium p-toluenesulfonate, cyclohexylmethyl(2-oxocyclohexyl)-sulfonium trifluoromethanesulfonate, cyclohexylmethyl(2oxocyclohexyl) sulfonium p-toluenesulfonate, dimethylphenyl-sulfonium trifluoromethanesulfonate, dimethylphenyl-sulfonium p-toluenesulfonate, dicyclohexylphenylsulfonium trifluoromethanesulfonate, dicyclohexylphenylsulfonium p-toluenesulfonate, trinaphthylsulfonium trifluoromethane-sulfonate, cyclohexylmethyl(2-oxocyclohexyl)sulfonium trifluoromethanesulfonate, (2-norbornyl)methyl(2-oxocyclo-hexyl)sulfonium trifluoromethanesulfonate, ethylenebis-[methyl(2-oxocyclopentyl)sulfonium trifluoromethane-sulfonate], 1,2'-naphthylcarbonylmethyltetrahydrothiophenium triflate, or mixtures thereof.

Photoacid catalysts may include diazomethane derivatives such as, for example, bis(benzenesulfonyl)-diazomethane, bis(p-toluenesulfonyl)diazomethane, bis(xylenesulfonyl)diazomethane, bis(cyclohexylsulfonyl)-diazomethane, bis(cyclopentylsulfonyl)diazomethane, bis(n-butylsulfonyl) diazomethane, bis(isobutylsulfonyl)-diazomethane, bis(sec-butylsulfonyl)diazomethane, bis(n-propylsulfonyl)diazomethane, bis(isopropylsulfonyl)-diazomethane, bis(tert-butylsulfonyl)diazomethane, bis(n-amylsulfonyl) diazomethane, bis(isoamylsulfonyl)-diazomethane, bis(sec-amylsulfonyl)diazomethane, bis(tert-amylsulfonyl) diazomethane, 1-cyclohexylsulfonyl-1-(tert-butylsulfonyl) diazomethane, 1-cyclohexylsulfonyl-1-(tert-amylsulfonyl) diazomethane, 1-tert-amylsulfonyl-1-(tert-butylsulfonyl) diazomethane, or mixtures thereof.

Photoacid catalysts may include glyoxime derivatives such as, for example, bis-o-(p-toluenesulfonyl)-α-dimethylglyoxime, bis-o-(p-toluenesulfonyl)-α-diphenylglyoxime, bis-o-(p-toluenesulfonyl)-α-dicyclohexyl-glyoxime, bis-o-(p-toluenesulfonyl)-2,3-pentanedione-glyoxime, bis-o-(p-toluenesulfonyl)-2-methyl-3,4-pentane-dioneglyoxime, bis-o-(n-butanesulfonyl)-α-dimethylglyoxime, bis-o-(n-butanesulfonyl)-α-diphenylglyoxime, bis-o-(n- butanesulfonyl)-α-dicyclohexylglyoxime, bis-o-(n-butanesulfonyl)-2,3-pentanedioneglyoxime, bis-o-(n-butanesulfonyl)-2-methyl-3,4-pentanedioneglyoxime, bis-o-(methanesulfonyl)-α-dimethylglyoxime, bis-o-(trifluoromethanesulfonyl)-α-dimethylglyoxime, bis-o-(1,1,1-trifluoroethanesulfonyl)-α-dimethylglyoxime, bis-o-(tert-butanesulfonyl)-α-dimethylglyoxime, bis-o-(perfluorooctanesulfonyl)-α-dimethylglyoxime, bis-o-(cyclohexane-sulfonyl)-α-dimethylglyoxime, bis-o-(benzenesulfonyl)-α-dimethylglyoxime, bis-o-(p-fluorobenzenesulfonyl)-α-dimethylglyoxime, bis-o-(p-tert-butylbenzenesulfonyl)-α-dimethylglyoxime, bis-o-(xylenesulfonyl)-α-dimethylglyoxime, bis-o-(camphorsulfonyl)-α-dimethylglyoxime, or mixtures thereof.

Photoacid catalysts may include bissulfone derivatives such as, for example, bisnaphthylsulfonylmethane, bistrifluoromethylsulfonylmethane, Bismethylsulfonylmethane, bisethylsulfonylmethane, bispropylsulfonylmethane, bisisopropylsulfonylmethane, bis-p-toluenesulfonylmethane, bisbenzenesulfonylmethane, 2-cyclohexyl-carbonyl-2-(p-toluenesulfonyl)propane (β-ketosulfone derivative), 2-isopropyl-carbonyl-2-(p-toluenesulfonyl) propane (β-ketosulfone derivative), or mixtures thereof.

Photoacid catalysts may include disulfono derivatives such as, for example, diphenyl disulfone, dicyclohexyl disulfone, or mixtures thereof.

Photoacid catalysts may include nitrobenzyl sulfonate derivatives such as, for example, 2,6-dinitrobenzyl p-toluenesulfonate, 2,4-dinitrobenzyl p-toluenesulfonate, or mixtures thereof.

Photoacid catalysts may include sulfonic acid ester derivatives such as, for example, 1,2,3-tris(methanesulfonyloxy)benzene, 1,2,3-tris(trifluoro-methanesulfonyloxy)benzene, 1,2,3-tris(p-toluenesulfonyloxy)benzene, or mixtures thereof.

Photoacid catalysts may include sulfonic acid esters of N-hydroxyimides such as, for example, N-hydroxysuccinimide methanesulfonate, N-hydroxysuccinimide trifluoromethanesulfonate, N-hydroxysuccinimide ethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide 1-octanesulfonate, N-hydroxysuccinimide p-toluenesulfonate, N-hydroxysuccinimide p-methoxybenzenesulfonate, N-hydroxysuccinimide 2-chloroethanesulfonate, N-hydroxysuccinimide benzenesulfonate, N-hydroxysuccinimide 2,4,6-trimethyl-benzenesulfonate, N-hydroxysuccinimide 1-naphthalenesulfonate, N-hydroxysuccinimide 2-naphthalenesulfonate, N-hydroxy-2-phenylsuccinimide methanesulfonate, N-hydroxymaleimide methanesulfonate, N-hydroxymaleimide ethane-sulfonate, N-hydroxy-2-phenylmaleimide methanesulfonate, N-hydroxyglutarimide methanesulfonate, N-hydroxyglutarimide benzenesulfonate, N-hydroxyphthalimide methanesulfonate, N-hydroxyphthalimide benzenesulfonate, N-hydroxyphthalimide trifluoromethanesulfonate, N-hydroxyphthalimide p-toluenesulfonate, N-hydroxynaphthalimide methanesulfonate, N-hydroxynaphthalimide benzenesulfonate, N-hydroxy-5-norbornene-2,3-dicarboxyimide methanesulfonate, N-hydroxy-5-norbornene-2,3-dicarboxyimide trifluoromethanesulfonate, N-hydroxy-5-norbornene-2,3-dicarboxyimide p-toluenesulfonate, N-hydroxynaphthalimide triflate, N-hydroxy-5-norbornene-2,3-dicarboximide perfluoro-1-butanesulfonate, or mixtures thereof.

Photoacid catalysts may also include fluoresceins and derivatives thereof; preferably halogen substituted fluoresceins; more preferably bromo- and iodo-fluoresceins such as dibromo fluorescein, diodo fluorescein, rose bengal, erythrosine, eosin (e.g. Eosin Y);

Hydroxy flavones and derivatives thereof; preferably hydroxyl flavones, dihydroxy flavones, trihydroxy flavones, tetrahydroxy flavones; more preferably 3-hydroxy flavones, 7-hydroxy flavones, 5,7-hydroxy flavones, 4',5,7-trihydroxy flavone, and quercitin;

Hydroxyl triarylmethanes, preferably FD&C Green 3;

Anthocyanidins and anthocyanins; preferably cyanidin, malvidin, palargonidin and extracts containing anthocyanins such as elderberry, blueberry, cranberry, bilberry, red cabbage, sorghums, blackberry, black current, cherry red and black raspberry.

In some aspects, the photocatalyst is 8-hydroxyquinoline, which may act as a photoacid catalyst in lower pH solutions or as a photobase catalyst in higher pH solutions. In other aspects, the photocatalyst is 8-hydroxy-1,3,6-pyrentrisulfonic acid trisodium salt (D&C Green 8).

In some aspects, the photocatalyst is a photobase. Photobase catalysts may include derivatives of trityl alcohols such as, for example, Malachite green. Photobase catalysts may also include acridine derivatives such as, for example, 9-hydroxy-10-methyl-9-phenyl-9,10-dihydroacridine. Photobase catalysts may also include photoactive carbamate-containing compounds.

The photocatalyst may be present in the compositions and methods described herein in an amount from about 0.00050% to 30%, from about 0.01% to about 15%, from about 0.01% to about 10%, or from about 0.01% to about 5%, by weight of the treatment composition. Generally, there is a preferred concentration of the photocatalyst. The preferred concentration of photocatalyst depends, in part, on a variety of factors including, for example, the chemical structure of the catalyst, the reaction medium, the reaction type, the type of fibrous material, and whether the treatment composition is diluted before/during use in the methods of the present invention.

Carrier

The compositions described herein optionally, and preferably, further comprise a carrier suitable for carrying, dispersing or dissolving the active agent, the photocatalyst, and any other components to facilitate making the treatment composition and/or application of the treatment composition onto the fibrous material. The carrier may comprise one or more of a solvent, an emulsifier, a surfactant, or other dispersant. The carrier may also be a physiologically-acceptable carrier. The properties of a suitable carrier are dependant, at least in part, on the properties of the other components of the composition and the substrate to be modified.

A suitable carrier operates to disperse or dissolve the active material, the photocatalyst, and any other components, and to facilitate application of the composition onto the substrate surface. A suitable carrier facilitates sufficient contact between the active material and the substrate. In various embodiments, a physiologically-acceptable carrier may be any carrier, solvent, or solvent-containing composition that is suitable for application to physiological tissues such as human hair and human skin, for example, in the context of personal care products. In various embodiments, a physiologically-acceptable carrier is a cosmetically- or dermatologically-acceptable carrier.

A suitable carrier may be a solvent. In personal and household care product applications, for example, water is a useful solvent. In various embodiments, the compositions described herein may include water in an amount from 1% to 98% by weight relative to the total weight of the composition. Water is also a physiologically acceptable carrier. Additional solvent or solvent-containing physiologically-acceptable carriers include, but are not limited to, hydroxyl-containing liquids (e.g., alcohols), silicones, oils, hydrocarbons, glycols, and combinations thereof. In certain embodiments, for example, where the active material is at least partially insoluble in water, other solvents, dispersants, or emulsifiers may be used as physiologically-acceptable carriers, alone or in combination with each other and/or with water.

Alcohols, such as ethanol, can be useful carriers, especially for assisting in solubilizing the active agent and/or photocatalyst.

A suitable carrier is therefore generally used to dilute and/or emulsify the components forming the compositions described herein. A suitable carrier may dissolve a component (true solution or micellar solution) or a component may be dispersed throughout the carrier (suspension, dispersion or emulsion). The carrier of suspension, dispersion or emulsion may be the continuous phase thereof, in which other components of the suspension, dispersion or emulsion are distributed on a molecular level or as discrete or agglomerated particles throughout the carrier. The preparation of such emulsions or dispersions of the active in these cases may be highly important. Small particles contribute to an intimate contact between the active, the substrate and the photoacid catalyst, increasing the reaction rate.

It will be readily apparent to one of ordinary skill in the art that the appropriate carrier(s) are dependent upon the specific active agent(s), photocatalyst(s), and other optional component(s) used in the compositions described herein.

Optional Components

The treatment compositions and methods described herein may optionally include a variety of components, which will depend on the nature of the treatment composition. The treatment composition is preferably a consumer product composition, more preferably a personal care product composition or a household care composition. For example, in various aspects, the treatment compositions and methods described herein may include surfactants, emulsifiers, oxidants, reductants, pH regulators, emollients, humectants, proteins, peptides, amino acids, additive polymers, glossers, oils and/or fatty acids, lubricants, sequestrants/chelators, antistatic agents, rheology modifiers, feel agents, fillers, dyes, preservatives, perfumes, other functional components, or combinations thereof. Particular optional components may be found in the CTFA International Cosmetic Ingredient Dictionary, Tenth Edition, 2004; and in McCutcheon, Detergents and Emulsifiers, North American Edition (1986). It will be readily apparent to one of ordinary skill in the art that the particular optional components utilized will be dependant, at least in part, upon the specific applications for the compositions and methods.

Non-limiting examples of treatment compositions, in which the active agent and photocatalyst can be incorporated, include:

liquid laundry detergents, such as those described in detail in US 2012/0324653 A1;

granular laundry detergents, such as those described in detail in U.S. Pat. No. 7,605,116;

unit dose laundry detergents, such as those described in detail in WO 2013/039964 A1, WO 2006/057905 A1, WO 2006/130647 A1;

liquid fabric softeners, such as those described in detail in U.S. Pat. No. 7,135,451, U.S. Pat. No. 6,369,025 and U.S. Pat. No. 6,492,322;

dryer-added fabric softener sheets, such as those described in detail in U.S. Pat. No. 6,787,510;

fabric treatment sprays, such as those described in detail in U.S. Pat. No. 5,939,060, WO 01/88076, US 2009/0038083 A1, and U.S. Pat. No. 6,573,233;

hair shampoos, such as those described in detail in US 2013/0080279 A1;

hair conditioners, such as those described in detail in U.S. Pat. No. 8,017,108;

hair styling compositions, such as those described in detail in US 2009/0061004 and EP2570192;

cosmetics, including mascara compositions, such as those described in detail in US 2012/0114585.

The treatment compositions of the present invention can be in the form of a liquid composition or a solid composition (preferably a water-soluble solid composition). If in the form of a liquid composition, the liquid composition is preferably packaged in an opaque package, and/or a package which blocks electromagnetic radiation at a wavelength which activates the photocatalyst of the treatment composition (which does not necessarily have to be an opaque package), to prevent the premature photoactivation of the treatment composition. Solid compositions can be preferred as solid compositions tend not to prematurely photoactivate until contacting aqueous solutions. Solid compositions are also preferably packaged in opaque packages to further prevent premature photoactivation. If in the form of a solid composition, the solid composition is preferably dissolved in a carrier, such as water, before being applied to the fibrous material.

In at least one aspect, the treatment composition is substantially free of, or completely free of, formaldehyde, derivatives of formaldehyde, methylene glycol, formalin, and any compound that produces formaldehyde upon heating. "Heating" means raising the temperature of the compound above 25° C. In at least one aspect, the treatment composition is substantially free of, or completely free of, a quaternary ammonium compound and/or a surfactant. In at least one aspect, the treatment composition is substantially free of, or completely free of, a ceramide compound, an alpha-hydroxy acid, a thioglycolate and/or thiolactate compound, a bisulfate compound, clay, and/or a reducing agent. In at least one aspect, the treatment composition is substantially free of, or completely free of, a carbonate compound.

Methods for Shaping Fibrous Material

The present invention further encompasses a method for shaping fibrous material comprising the steps of providing a treatment composition comprising an active agent and a photocatalyst, applying the treatment composition to the fibrous material to form a treated fibrous material, mechanically shaping the treated fibrous material, and exposing the treated fibrous material to electromagnetic radiation. Suitable treatment compositions include those described hereinbefore. It should be noted that the step of applying the treatment composition to the fibrous material and the step of mechanically shaping the fibrous material can be carried out in either order.

The treated fibrous material is exposed to electromagnetic radiation preferably having a wavelength of from about 300 nm to about 750 nm. In at least one aspect, the electromagnetic radiation has a wavelength of from about 310 nm, from about 320 nm, from about 330 nm, from about 340 nm, from about 350 nm, from about 360 nm, from about 370 nm, from about 380 nm, from about 390 nm, from about 400 nm, or from about 410 nm, to about 740 nm, to about 730 nm, to about 720 nm, to about 710 nm, to about 700 nm, to about 690 nm, to about 680 nm, to about 670 nm, to about 650 nm, or to about 640 nm. In at least one aspect, the electromagnetic radiation has a wavelength of from 380 nm to about 550 nm.

The electromagnetic radiation can be provided by a light source selected from the group consisting of: ambient light, sunlight, incandescent light, fluorescent light, LED light, laser light, solar light, and combinations thereof. The electromagnetic radiation is preferably visible light. The light can be provided by conventional sources such as lamps and portable or battery-powered lights. Specific devices may be developed or adapted for use with the treatment compositions and methods described herein. For example, an appliance can be configured to incorporate LEDs as a light source. In at least one aspect, the light source is a laser light. A laser may be used to provide precise targeting, for example. In at least one aspect, the appliance is a hybrid heat- and light-providing hair straightening iron.

The treated fibrous material can be mechanically shaped by creasing, curling, straightening, flattening, or otherwise changing the physical orientation of the fibrous material.

The methods of the present invention can optionally further comprise the step of heating the fibrous material. The heating step can elevate the temperature of the fibrous material to a temperature of from about 40° C. to about 150° C. The heating step can comprise elevating the temperature of an implement or appliance to a temperature of from about 40° C., or from about 60° C., or from about 70° C., or from about 80° C. to about 220° C., or to about 200° C., or to about 180° C., or to about 170° C., or to about 160° C., or to about 150° C., or to about 140° C., or to about 130° C., and then contacting the fibrous material with the implement or appliance to elevate the temperature and/or mechanically shape the fibrous material.

In the methods of the present invention, the treatment composition is preferably not exposed to electromagnetic radiation of less than 750 nm for a period of at least 1 second, at least 1 minute, at least 5 minutes, at least 10 minutes, or at least 30 minutes, before the step of applying the treatment composition to the fibrous material.

Implement

The methods of the present invention can utilize an implement to mechanically shape the fibrous material, to provide electromagnetic radiation, and/or to provide heat. With respect to mechanically shaping the fibrous material, the implement can be any appliance, device, or appendage by use of which the fibrous material can be shaped. For example, the implement can be a hair straightening appliance. The hair straightening appliance can comprise a light source and/or a heating element. Suitable hair straightening appliances are described in detail in "APPLIANCE FOR SHAPING FIBROUS MATERIAL", R. P. Washington et al., U.S. Application Ser. No. 61/918,159. Such an appliance comprises a light source that provides electromagnetic radiation and a heating element. This type of appliance can be used to mechanically shape the fibrous material, provide electromagnetic radiation, and provide heat (e.g. an all-in-one appliance).

The implement can also be a device, such as the fabric tensioning apparatus described in US 2010/0282785 A1. The implement can also be a plate, such as a plexiglass plate, which can mechanically shape (e.g. to flatten or straighten) the fibrous material upon application of pressure.

The implement can comprise a light source to provide electromagnetic radiation for the method of the present invention.

The implement can also be an appendage, such as a finger or hand. In this regard, the fibrous material can be mechanically shaped by the consumer manually manipulating the fibrous material using her fingers or hands.

Kits

The present invention further relates to a kit comprising a treatment composition comprising an active agent and a photocatalyst, and an appliance for mechanically shaping a fibrous material, for providing electromagnetic radiation, and/or for providing heat. Treatment compositions and appliances suitable for use in the kits of the present invention are described hereinbefore.

Examples

The following examples are intended to more clearly illustrate aspects of the compositions and methods described herein, but are not intended to limit the scope thereof. The amounts provided are weight percentages, unless otherwise indicated.

Treatment Compositions

|  | A | B | C | D | E[4] |
|---|---|---|---|---|---|
| Arabinose | — | 10 | 10 | 1 | 41.6 (5) |
| Ribose | 5 | — | 10 | 1 | 8.32 (1) |
| Xylose | — | — | — | 1 | 8.32 (1) |
| 8-hydroxyquinoline | 0.01 | — | — | 0.01 | 0.08 (0.01) |
| 7-cyano-2-naphthol | — | 0.005 | — | — | — |
| 8-quinolinol-1-oxide | — | — | 0.01 | 0.01 | 0.08 (0.01) |
| Preservatives [1] | 1 | 1 | 1 | 1 | 8.32 (1) |
| Fragrance | 2 | 2 | 2 | 2 | 16.64 (2) |
| Viscosity-modifying agent [2] | 2 | 2 | 2 | 2 | 16.64 (2) |
| Conditioning agent [3] | 1 | 1 | 1 | 1 | — |
| Deionised water | QSP | QSP | QSP | QSP | — |

[1] Sodium benzoate
[2] Acusol 823 available from Rohm & Haas
[3] Epoxyaminosilane copolymer available from Momentive Performance Materials Inc.
[4] Example E is a solid treatment composition; the weight percent values in parenthesis reflect amounts after the solid composition is dissolved in water

|  | 1 | 2 | 3 | 4 | 5 | 6 | 7 |
|---|---|---|---|---|---|---|---|
| Arabinose | 5 | — | — | — | — | — | — |
| Ribose | — | 5 | — | — | — | — | — |
| Xylose | — | — | 5 | — | — | — | — |
| Mannose | — | — | — | 5 | — | — | — |
| Glucose | — | — | — | — | 5 | — | — |
| Fructose | — | — | — | — | — | 5 | — |
| Sucrose | — | — | — | — | — | — | 5 |
| 8-hydroxyquinoline | 0.01 | 0.01 | 0.01 | 0.01 | 0.01 | 0.01 | 0.01 |
| 8-quinolinol-1-oxide | 0.01 | 0.01 | 0.01 | 0.01 | 0.01 | 0.01 | 0.01 |
| Deionised water | QSP | QSP | QSP | QSP | QSP | QSP | QSP |

|  | F | G | H | I |
|---|---|---|---|---|
| Glucose | 5 | 15 | 25 | — |
| Arabinose | — | — | — | 15 |
| 8-quinolinol-1-oxide | 0.01 | 0.01 | 0.01 | 0.01 |
| Deionised water | QSP | QSP | QSP | QSP |

Hair Straightening

The hair straightening efficacy is evaluated using the following test method. Switches of low lift naturally curly hair are employed. These are shampooed with a Pantene clarifying shampoo to ensure the hair is in a clean state with no residues that could affect the end result. The switches are then rinsed. Excess water is removed from the hair by wringing out the switches. The switches are treated with a treatment composition of the present invention which is pre-prepared in a dark room and buffered at pH 10. The ingredients of the treatment composition are mixed on a spinner plate for 30 mins. The treatment composition is stored in an amber bottle or a bottle covered in electrical tape to ensure no light access to the treatment composition. 0.25 g of treatment composition per 1 g hair is employed. The treatment composition is left on the hair for 30 minutes. As a control, hair switches are treated exactly the same but no treatment composition is applied to the switch—the control switches are allowed to rest damp for 30 minutes. After this time, the hair is blow dried and brushed. The switches are then mechanically straightened with a hybrid light- and heat-emitting straightening iron with 8 passes. The switches are then imaged. To simulate durability, the switches are then given one wash-and-dry cycle. One wash-and-dry cycle involves shampooing with a Hairtrition shampoo (Hairtrition Color Protect sulfate-free shampoo from Zotos), rinsing and then drying in a hot box. Once dry the switches are imaged again. The switches are then given 4 further wash-and-dry cycles. Once dry the switches are imaged again. An expert grader gives the images of the switches a score on a 0-10 scale. The scale is a standard scale set as curly hair having 4-5 nodes of curls is a score of 0 and very straight hair is a 10. Thus, the switches are compared to a normal state of hair. Using an expert grader is reliable because the grader is trained on measuring/scaling the configuration of the hair from straight to curly in a consistent way.

Treatment compositions according to Examples 1, 2, 3, 4, 5, 6, and 7 above are evaluated, along with a control ("C"), according to the test method above. The results are reported as a bar chart in FIG. 1. In the bar chart, the y axis is the straightness score (10 is very straight and 0 is very curly). In the bar chart, the bars with the diagonal shading lines show the straightness score by the expert grader after one wash-and-dry cycle and the bars with the horizontal shading lines show the straightness score by the expert grader after five wash-and-dry cycles. As shown in the bar chart in FIG. 1, the treatment compositions of the present invention show excellent hair straightening benefit versus a control where no treatment composition is used. The hair straightening benefit is durable in that the benefit is seen following one wash-and-dry cycle.

Figure 2:
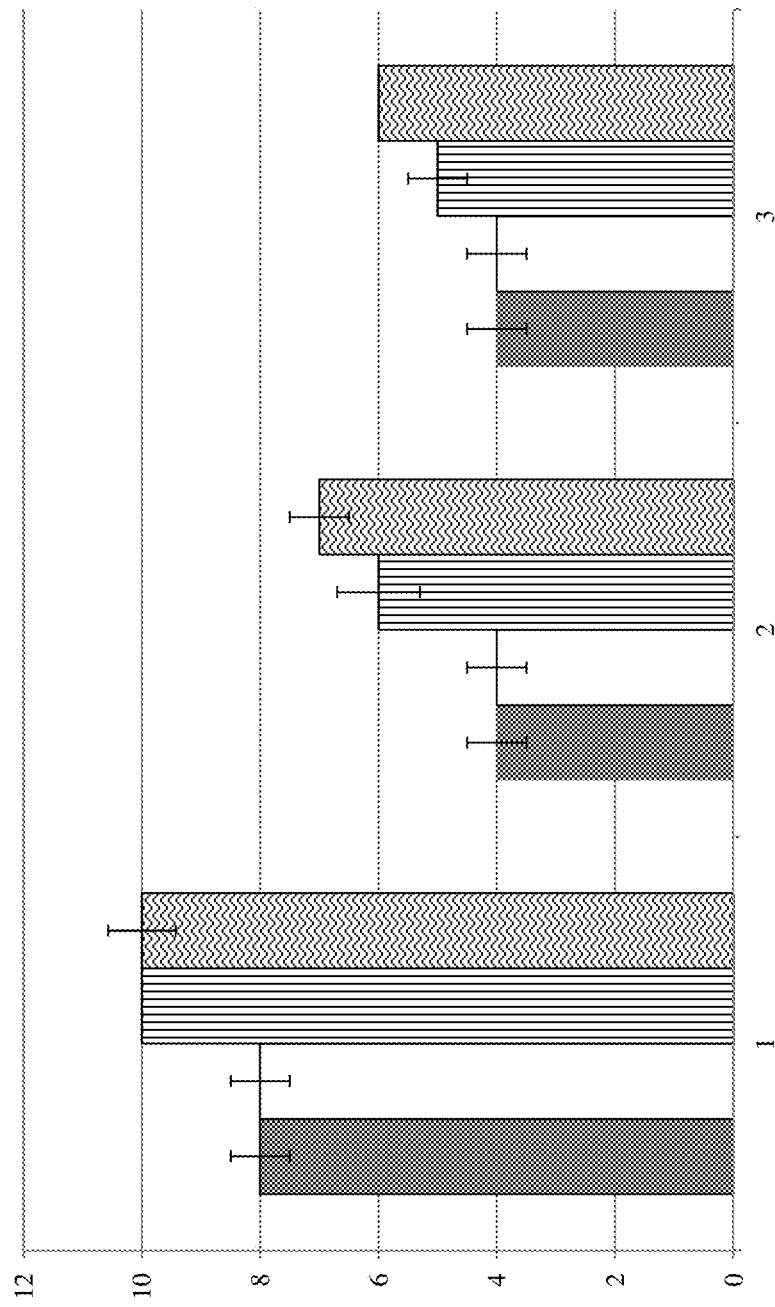
FIG. 2 is a bar chart illustrating hair straightening results for a treatment composition of the present invention under various conditions versus a control.

In shown in FIG. 2, hair straightening effects via the use of heat and/or UV light are evaluated using the treatment composition of Example 1 in the test method above, but under different conditions. As shown in FIG. 2, the numbering along the x axis of the bar chart in FIG. 2 refers to the following: 1=immediately after the flat iron treatment; 2=after the 1$^{st}$ wash-and-dry cycle; 3=after the 5$^{th}$ (i.e. 4 further) wash-and-dry cycles. The data reflected by the black bars in FIG. 2 relate to using no treatment composition and treating the hair switches with a hair straightening iron at 250° F. (121° C.). The data reflected by the grey bars in FIG. 2 relate to using no treatment composition and treating the hair switches with a hybrid heat and UV light hair straightening iron at 250° F. (121° C.). In FIG. 2, the horizontal-striped bars reflect hair switches that are treated with a treatment composition of Example 1 buffered at pH 10 and treating the hair switches with a heated hair straightening iron at 250° F. (121° C.). In FIG. 2, the wavy-striped bars reflect hair switches that are treated with a treatment composition of Example 1 buffered to pH 10 and treating the hair switches with a hybrid heat and UV light hair straightening iron at 250° F. (121° C.).

Eyelash Shaping

Figure 3:
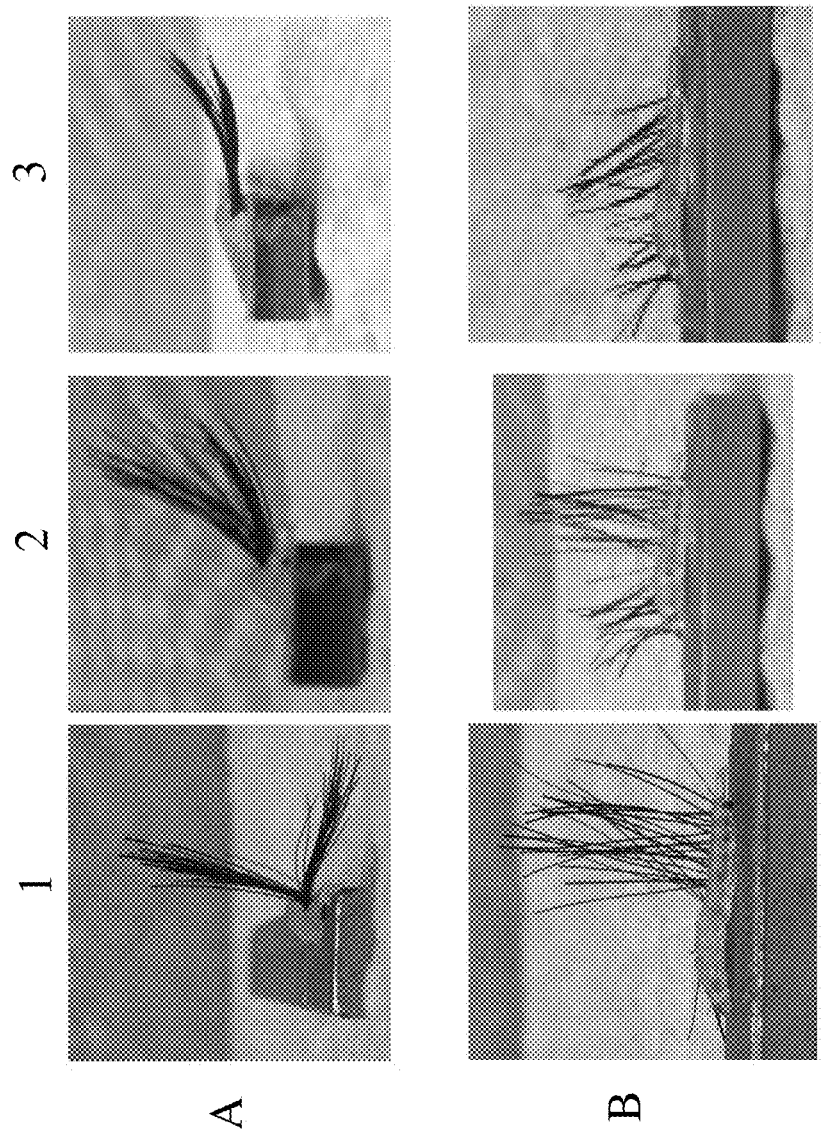
FIG. 3 is a series of photographs illustrating eyelash shaping results for a treatment composition of the present invention.

The ability to shape eyelashes is evaluated using the following procedure. The eyelashes used are artificial eyelashes that are made from scalp hair glued to a bar and artificially shaped and dried to look like eyelashes. The eyelashes are bent out of shape. Firstly, the eyelashes are washed with a clarifying shampoo to get them clean and remove any residue. The eyelashes are soaked in a treatment composition consisting of 20% arabinose; 100 ppm 8-hydroxyquinoline; 100 ppm 8-quinolinol-1-oxide; and QSP water buffered at pH 10. The eyelashes are submerged overnight in the treatment composition. Afterwards, the eyelashes are shaped, for example by pulling the lashes straight with tweezers or by curling them. After this stage, the 'back' half of the eyelashes are wrapped in foil. The eyelashes are then exposed to light (UV LEDs) for 1 min. The portion of eyelashes wrapped in foil do not receive any UV light. The eyelashes are wiped with an OLAY facial wipe to simulate a consumer washing step. The eyelashes are then further wiped with OLAY facial wipes to simulate a further consumer washing steps. The eyelashes are imaged at various points in the process. In FIG. 3, the results of these experiments can be seen. The images in column 1 of FIG. 3 are taken immediately after treatment, in column 2 after 1 wash, and in column 3 after 5 washes. In row A of FIG. 3, the half of the eyelash nearest the camera received the UV light. Row B of FIG. 3 is the same eyelash taken from a different angle (the right-hand half of the eyelash received the UV light). As shown in the images of FIG. 3, the portion of the eyelash that was exposed to UV light shows significantly more durable shaping than the portion of the eyelash that was not exposed to UV light.

Reducing Wrinkles in Fabric

The following test method is utilized to evaluate the ability of a treatment composition of the present invention to reduce the appearance of wrinkles in fabric. Dress shirts are obtained from Land's End Company as Men's Regular Long Sleeve Button-down Solid Pinpoint Shirt in Size Large (Item #245195). The dress shirts are washed, rinsed and dried in a conventional automatic washer/dryer and allowed to rest in the bottom of the dryer prior to treatment.

100 g of a treatment composition is sprayed from a manual spray bottle evenly onto the dress shirt. The treated shirt is mechanically shaped using a fabric tensioning apparatus as described in US 2010/0282785 A1. Using only the fabric tensioning apparatus as described in US 2010/0282785 A1 (and not using the other components of the fabric treating system described therein), the treated shirt is allowed to air dry. Once dry, the shirt is visually graded against a control, as described below. The control is the same type of dress shirt prepared and treated identically with the exception that 100 g of water is used in place of the 100 g of treatment composition.

Visual grading is performed by at least 4 visual-graders against the scale depicted below, with the final grade being reported as the average of the individual grades.

| Grade | Visual Assessment of Wrinkling |
| --- | --- |
| −2 | Much more wrinkled than control |
| −1 | More wrinkled than Control |
| 0 | Equal to control |
| 1 | Less wrinkled than Control |
| 2 | Much less wrinkled than Control |

The treatment compositions of Examples F, G, H, and I are each tested according to the test method above, resulting in the following grades:

| Treatment Composition | Grade |
|---|---|
| Example F | 1.9 |
| Example G | 1.9 |
| Example H | 2.0 |
| Example I | 2.0 |

These results indicate that the treatment compositions provide greater wrinkle reduction as compared to the control (i.e. water only).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for shaping fibrous material comprising:
   (a) providing a treatment composition, wherein the treatment composition comprises:
      (i) an active agent comprising a sugar; and
      (ii) a photocatalyst;
   (b) applying the treatment composition to a fibrous material to form a treated fibrous material;
   (c) mechanically shaping the treated fibrous material by using an implement; and
   (d) exposing the treated fibrous material to electromagnetic radiation.

2. The method of claim 1, wherein said active agent has a molecular weight below about 1000 g/mol.

3. The method of claim 1, wherein the electromagnetic radiation has a wavelength of from about 300 nm to about 750 nm.

4. The method of claim 1, wherein the photocatalyst is a photoacid.

5. The method of claim 4, wherein the photoacid is a hydroxyl-substituted aromatic compound.

6. The method of claim 1, wherein the implement comprises a light source.

7. The method of claim 6, wherein the light source is selected from the group consisting of incandescent light, fluorescent light, LED light, laser light, solar light, and combinations thereof.

8. The method of claim 1, wherein the treatment composition has not been exposed to electromagnetic radiation having a wavelength of less than 750 nm for a period of at least 1 second before the step of applying the treatment composition to the fibrous material.

9. The method of claim 1, wherein the photocatalyst is selected from the group consisting of: 8-hydroxyquinoline, 8-hydroxyquinoline sulfate, 8-quinolinol-1-oxide, 5-hydroxyquinoline, 6-hydroxyquinoline, 7-hydroxyquinoline, 5-iodo-7-sulfo-8-hydroxyquinoline, 5-fluoro-8-hydroxyquinoline, 5-fluoro-7-chloro-8-hydroxyquinoline, 5-fluoro-7-bromo-8-hydroxyquinoline, 5-fluoro-7-iodo-8-hydroxyquinoline, 7-fluoro-8-hydroxyquinoline, 5-chloro-8-hydroxyquinoline, 5,7-dichloro-8-hydroxyquinoline, 5-chloro-7-brono-8-hydroxyquinoline, 5-chloro-7-iodo-8-hydroxyquinoline, 7-chloro-8-hydroxyquinoline, 5-bromo-8-hydroxyquinoline, 5-bromo-7-chloro-8-hydroxyquinoline, 5,7-dibromo-8-hydroxyquinoline, 5-bromo-7-iodo-8-hydroxyquinoline, 7-bromo-8-hydroxyquinoline, 5-iodo-8-hydroxyquinoline, 5-iodo-7-chloro-8-hydroxyquinoline, 5,7-diiodo-8-hydroxyquinoline, 7-iodo-8-hydroxyquinoline, 5-sulfonic acid-8-hydroxyquinoline, 7-sulfonic acid-8-hydroxyquinoline, 5-sulfonic acid-7-iodo-8-hydroxyquinoline, 5-thiocyano-8-hydroxyquinoline, 5-chloro-8-hydroxyquinoline, 5-bromo-8-hydroxyquinoline, 5,7-dibromo-8-hydroxyquinoline, 5-iodo-8-hydroxyquinoline, 5,7-diiodo-8-hydroxyquinoline, 7-azaindole, 7-cyano-2-naphthol, 8-cyano-2-naphthol, 5-cyano-2-naphthol, 1-hydroxy-3,6,8-pyrenetrisulfonic acid, trans-3-hydroxystilbene, 2-hydroxymethylphenol, Pelargonidin, and mixtures thereof.

10. The method of claim 1, wherein the fibrous material is selected from the group consisting of keratin fibers, cellulosic fibers, synthetic fibers, and combinations thereof.

11. The method of claim 1, wherein the fibrous material is keratin fibers.

12. The method of claim 1, wherein the fibrous material is a woven or nonwoven fabric.

13. The method of claim 1, wherein the method further comprises elevating the temperature of the treated fibrous material to a temperature of from about 40° C. to about 150° C.

14. The method of claim 1, wherein the implement further comprises a heat source.

15. The method of claim 1, wherein the treatment composition is substantially free of formaldehyde, derivatives of formaldehyde, formalin, and any compound that produces formaldehyde upon heating.

16. The method of claim 1, wherein the treatment composition comprises from about 0.1% to about 99.99%, by weight of the treatment composition, of the active agent.

17. The method of claim 1, wherein the treatment composition further comprises a carrier.

18. The method of claim 17, wherein the carrier is water.

19. The method of claim 1, wherein the treatment composition is a solid, and wherein the method further comprises the step of dissolving the treatment composition in a carrier.

20. The method of claim 1, wherein the active agent is a monosaccharide.

21. The method of claim 1, wherein said active agent is selected from the group consisting of ribose, arabinose, xylose, lyxose, galactose, mannose, glucose, and mixtures thereof.

22. The method of claim 1, wherein the active agent is arabinose.

23. The method of claim 1, wherein the treatment composition is packaged in an opaque package.

* * * * *